(12) United States Patent
Little et al.

(10) Patent No.: US 9,212,989 B2
(45) Date of Patent: Dec. 15, 2015

(54) OPTICAL DETERMINATION AND REPORTING OF GAS PROPERTIES

(75) Inventors: Paul Little, Austin, TX (US); Charles E. Miller, North Wales, PA (US)

(73) Assignee: JP3 Measurement, LLC, Austin, TX (US)

( * ) Notice: Subject to any disclaimer, the term of this patent is extended or adjusted under 35 U.S.C. 154(b) by 0 days.

(21) Appl. No.: 12/487,609

(22) Filed: Jun. 18, 2009

(65) Prior Publication Data
US 2010/0228688 A1   Sep. 9, 2010

Related U.S. Application Data

(63) Continuation-in-part of application No. 11/419,241, filed on May 19, 2006, now Pat. No. 9,057,718.

(60) Provisional application No. 60/761,981, filed on Jan. 25, 2006, provisional application No. 61/073,409, filed on Jun. 18, 2008, provisional application No. 60/724,025, filed on Oct. 6, 2005.

(51) Int. Cl.
| | |
|---|---|
| G01N 33/00 | (2006.01) |
| G01N 21/359 | (2014.01) |
| G01N 21/85 | (2006.01) |
| G01N 33/24 | (2006.01) |
| G06Q 50/06 | (2012.01) |
| G01N 21/3504 | (2014.01) |

(52) U.S. Cl.
CPC .......... *G01N 21/359* (2013.01); *G01N 21/3504* (2013.01); *G01N 21/85* (2013.01); *G01N 33/241* (2013.01); *G06Q 50/06* (2013.01)

(58) Field of Classification Search
CPC ............ G01N 21/3504; G01N 21/359; G01N 33/241; Y10T 436/21
USPC .......................................... 436/139; 705/413
See application file for complete search history.

(56) References Cited

U.S. PATENT DOCUMENTS

| | | | | |
|---|---|---|---|---|
| 6,157,455 | A * | 12/2000 | Pinvidic et al. ................ | 356/437 |
| 6,507,401 | B1 * | 1/2003 | Turner et al. .................. | 356/436 |
| 2003/0134426 | A1 * | 7/2003 | Jiang et al. ..................... | 436/121 |
| 2004/0204775 | A1 * | 10/2004 | Keyes et al. .................... | 700/29 |

OTHER PUBLICATIONS

Nielsen, Harold H. and Barker, Ernest F. "Infrared Absorption Bands in Hydrogen Sulphide," Physical Review, vol. 37, 1931, p. 727-732.*

* cited by examiner

*Primary Examiner* — Dennis M White
*Assistant Examiner* — Bryan Kilpatrick
(74) *Attorney, Agent, or Firm* — DuBois, Bryant & Campbell LLP; William D. Wiese

(57) ABSTRACT

A chemical composition analyzer may be used to optically determine and report chemical compositions associated with gases within a gas collection and transmission infrastructure. This analyzer includes a number of optical sensors which may be used to perform spectroscopic spectrographic analysis in order to determine the chemical composition of the gas. Additionally other sensors may be used to measure other physical properties associated with the gas. These sensors are tied to a data collection system wherein the output of the optical sensors and sensors used to measure the physical properties of the gas may be combined and processed in order to determine in a nearly continuous fashion the chemical composition associated with the gas at various locations within the gas collection and transmission infrastructure. This real time compositional analysis may be used to determine valuations of the gas or to optimize other processes or equipment configurations.

14 Claims, 19 Drawing Sheets

OPTICAL DETERMINATION AND REPORTING OF GAS PROPERTIES

RELATED APPLICATIONS

The present U.S. Utility Patent Application claims priority pursuant to 35 U.S.C. §119(e) to the following U.S. Provisional Patent Applications which are hereby incorporated herein by reference in their entirety and made part of the present U.S. Utility Patent Application for all purposes:

1. U.S. Provisional Application Ser. No. 61/073,409, entitled "OPTICAL DETERMINATION AND REPORTING OF GAS PROPERTIES," filed to inventor Paul Little.

The present U.S. Utility Patent Application claims priority pursuant to 35 U.S.C. §120, as a continuation-in-part (CIP), to the following U.S. Utility Patent Application which is hereby incorporated herein by reference in its entirety and made part of the present U.S. Utility Patent Application for all purposes:

1. U.S. Utility application Ser. No. 11/419,241, entitled "OPTICAL DETERMINATION AND REPORTING OF HYDROCARBON PROPERTIES," May 19, 2006 to inventor Paul Little, pending, which claims priority pursuant to 35 U.S.C. §119(e) to the following U.S. Provisional Patent Applications which are hereby incorporated herein by reference in its entirety and made part of the present U.S. Utility Patent Application for all purposes:

a. U.S. Provisional Application Ser. No. 60/724,025, entitled "Spectographic Analysis of Hydrocarbons," filed on Oct. 6, 2005 to inventor Paul Little.

b. U.S. Provisional Application Ser. No. 60/761,981, entitled "COMMUNICATION AND REPORTING OF OPTICALLY MEASURED PROPERTIES OF HYDROCARBONS," filed on Jan. 25, 2006 to inventor Paul Little.

TECHNICAL FIELD OF THE INVENTION

The present invention relates generally to chemical analysis systems and methods, and more particularly, a system and method to optically determine chemical properties of a gas.

BACKGROUND OF THE INVENTION

Current practices use gas chromatography (GC) to periodically sample natural gas to determine the chemical composition within a gas collection and transmission facility. For example, gas chromatography is often performed on a monthly or quarterly basis to determine the health of an individual well or field. These samples are then used to determine the quality, energy content, or pricing associated with the gas delivered from that well or field. However, changes in the gas content, for the better or worse, may result in unrealized profits from a well or field. In the case of declining quality, penalties may be imposed on the supplier by delivering product from a field that does not meet the previously stated product requirements. Thus, using only one sample to describe the quality of the gas for an entire quarter is unrealistic.

In another instance, these samples may be taken at a single gathering location which pools gases supplied from a number of wells or fields. As not all the wells may be on service at the time of the sample, the removal from service of a high energy well may adversely impact the measured quality. When the high energy well is returned to serve, the output from the gathering location may then be undervalued because for an entire quarter or until the next periodic sample. This is because the high energy content is not considered.

Additionally, the potentially large latency between samples may result in undetected rising levels of contaminants such as hydrogen sulfide, carbon dioxide, water, nitrogen, and other like contaminates that do not contribute to the energy content of the gas. This may result in the gases exceeding the specified levels during the periodicity between samples. This in turn may result in damage to processing or manufacturing equipment and fines for the supplier.

SUMMARY OF THE INVENTION

The present invention provides a system and method that substantially eliminates or reduces disadvantages and problems associated with previously developed chemical analysis systems and methods used to determine the content of natural gas.

The chemical composition of the natural gas within a gas collection and transmission infrastructure may be measured using optical sensors that perform spectrographic analysis. These sensors may be placed at various locations within the gas collection and transmission infrastructure and may be monitored locally or remotely. Additionally other sensors may be used to measure physical properties associated with the natural gas. The remote optical sensors and other sensors may be communicatively coupled to a data gathering location. This allows the sensors to report the chemical composition and physical properties associated with the natural gas. Processing modules within the data gathering location or having access to the data gathering location then may determine the chemical composition associated with the natural gas. In one embodiment, the present invention determines the energy content, specific gravity, compressibility, hydrogen dew point, moisture content, and Wobbe index of the natural gas which may then be used to determine the pricing structures or equipment configurations necessary to properly and efficiently process the natural gas.

A second embodiment, as alluded to previously, may be used to specifically determine the configuration of a natural gas processor module or other equipment associated with a natural gas collection, transmission and/or processing infrastructure. (i.e. The required scrubbing equipment may be identified based on the chemical composition of the natural gas.) As before the chemical composition of the natural gas may be measured using remote optical sensors that perform spectrographic analysis. Other properties (such as but not limited to pressure and temperature) associated with the natural gas may be determined as well. These remote sensors may be communicatively coupled to a data gathering location in order to report the chemical composition and physical properties associated with the natural gas. Having this information allows downstream processing and manufacturing equipment to be more efficiently or optimally configured in order to properly process the natural gas based on current market conditions, the end users needs, specifications, energy content, contaminants, or other qualities found in the chemical composition.

Another embodiment provides a chemical composition analyzer that may be used to optically determine and report the chemical composition of the natural gas within a gas collection and transmission infrastructure. This analyzer has a number of remote optical sensors that perform spectrographic analysis to measure or determine the chemical composition of the natural gas. Additionally other sensors may be used to measure the physical properties associated with the natural gas. Data collection and processing systems will couple to the sensors. This allows the output of the sensors to be processed using the data collection and processing system in order to determine in a real or quasi real time the chemical composition associated with the quantities of natural gas currently present within the gas collection and transmission infrastructure.

The information associated with determining the chemical composition of the natural gas may be used to schedule or identify the need for maintenance within the gas collection infrastructure. In one example this may be the need to further perforate a well. This may involve maintenance to the wells, handling equipment, or other maintenance or repair activities associated with the gas collection and processing infrastructure. Similarly, this knowledge of the chemical composition and other properties associated with the natural gas on a more frequent or continuous basis than was previously available allows one to properly and more accurately determine the energy content of the natural gas as it varies over time. This allows a more accurate pricing structure to be determined and implemented. Embodiments of the present invention also enable companies to characterize their reserves as the gas changes over time in order to derive a fair net present value and plan production.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Figure 1:
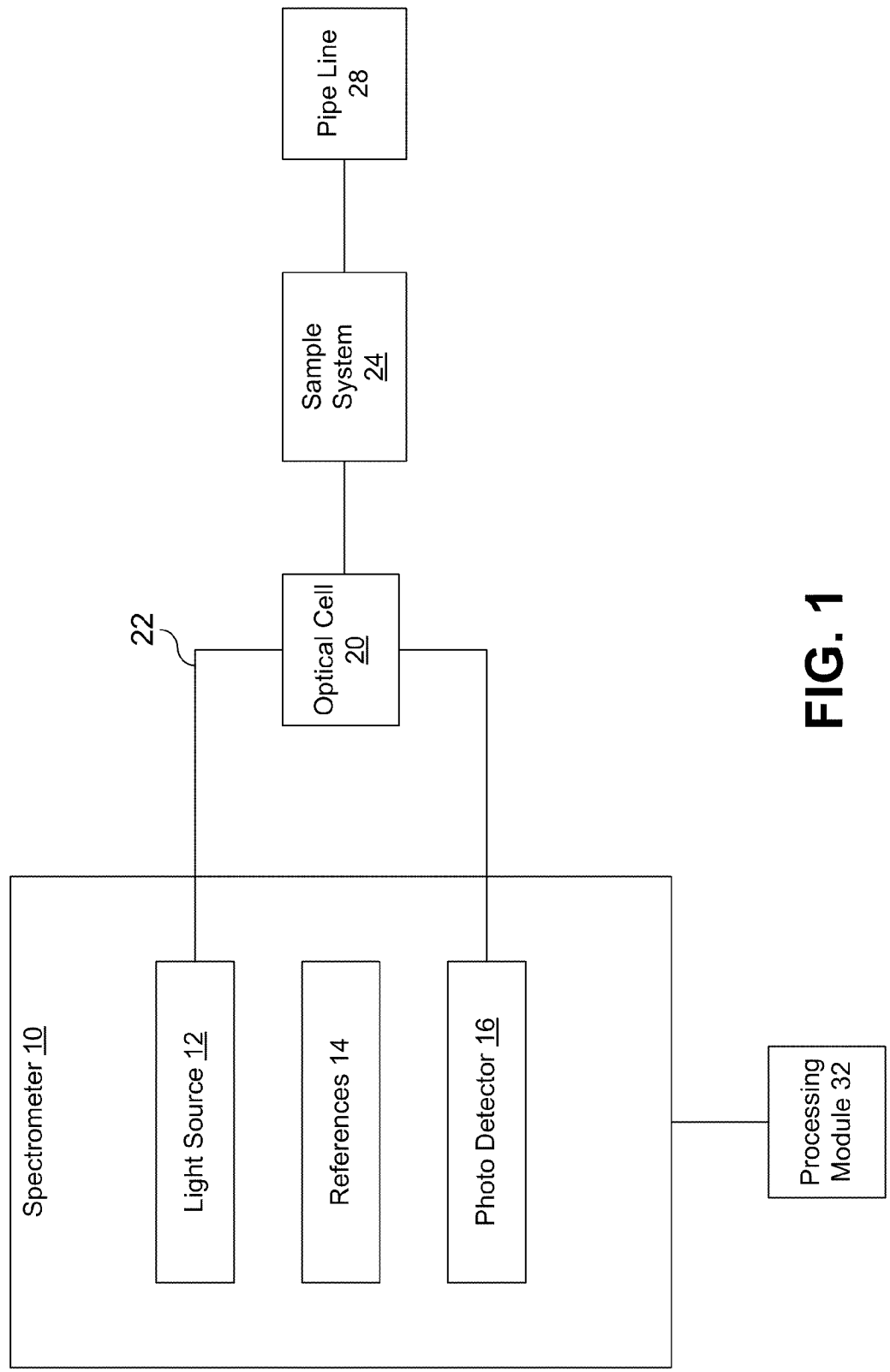
FIG. 1 provides a block diagram of a spectrometer operable to perform spectrographic analysis of gases in the field in accordance with an embodiment that may be used in accordance with an embodiment of the present invention.

Preferred embodiments of the present invention are illustrated in the FIGUREs, like numerals being used to refer to like and corresponding parts of the various drawings.

Embodiments of the present invention provide a way of optically determining the chemical composition of natural gas to derive the energy content (expressed in British Thermal Units (BTU)), hydrocarbon dew point, compressibility, specific gravity, moisture content, impurities, Wobbe index and other like properties associated with hydrocarbons such as but not limited to natural gas. Embodiments may employ the Near Infrared band of the electromagnetic spectrum, specifically between the 1300 nm to 2500 nm range. One embodiment focuses on the 1550 nm to 1800 nm range for the carbon hydrogen overtone to resolve the chemicals that contribute energy content to natural gas. Other embodiments may utilize 1350 nm to 1800 nm range to identify $CO_2$, $H_2S$ and other chemical components within the spectrum.

Another embodiment of the present invention provides a way of electronically gathering and reporting optically determined chemical compositions of natural gas including liquid natural gas. The invention describes an on-line process of gathering, transmitting, and storing data obtained using the NIR band of the electromagnetic spectrum, specifically between the 1300 nm to 2500 nm range. The information may be used to make various businesses, maintenance, and processing decisions based on the real-time feed or historically trended data from the instruments.

Micro-electromechanical machining processes have produced compact, reliable equipment capable of high resolution spectrographic analysis with very low power consumption. The low power consumption, small size, and readily available powerful micro-computing components enable these components to be remotely installed throughout a natural gas collection and transmission infrastructure. Gases, such as but not limited to natural gas are bought and sold based on volume and energy content.

Significant interest, especially at custody transfer points, exists in the ability to have a quick and accurate measurement of energy content, hydrocarbon dew point, compressibility, specific gravity, moisture content, and Wobbe index values. These installations will lead to a much more efficient and accurate market place.

NIR spectrographic analysis provides a non-invasive optical measurement that has no emissions. Further, there is no need for calibration gases or carrier gases to perform measurements as with traditional gas chromatography. Traditional remote site chromatographs need a calibration gas bottle and a carrier gas bottle approximately every 6 months. In addition to the consumable costs, the separation columns in the in the gas chromatographs (GCs) have a tendency to get clogged and need replacement. Unlike GCs, occasional liquid condensate introduction will not destroy expensive components in an NIR spectrometer. Therefore, NIR spectrographic analysis allows a more environmentally friendly and significantly cheaper cost of ownership than conventional chromatography.

An exemplary spectrometer 10 shown in FIG. 1 may be used by embodiments of the present invention includes a light source 12, integrated wavelength and amplitude references 14, and a photo detector 16. The light source 12 will preferably be a tunable diode laser. Spectrometer 10 will be coupled to an optical gas cell 20 via fiber optic cables 22. A sample system 24 will extract gas 26 from the pipe line 28, measure the pressure and temperature of the gas, direct the gas through optical cell 20 where it will be exposed to light from the light source 12, and reintroduce the sample in the transmission line 28 or exhaust it. The sample system may need to be heated in certain installations in order to keep the gas above the dew point temperature. The spectral data will be transmitted back to the photo detector 16 via the fiber optic cables 22. The detector array will preferably be an Indium Gallium Arsenide (InGaAs) photo detector. Electronics (processing module 32) will process the spectrographic image to determine the image's energy content and chemical composition. Other properties of the gas such as hydrocarbon dew point, specific gravity, compressibility, and Wobbe index can also be computed from the compositional information. The results will then be stored for a later transmission and analysis or sent directly to a data gathering location.

The processing module 32 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The memory may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processing module 32 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The processing module 32 executes, operational instructions corresponding to at least some of the steps and/or functions illustrated in FIG. 6.

Embodiments of the present invention may employ chemometeric models and other analytical techniques to determine the composition of the gas 26. The data models are used to compare the spectrums being gathered by spectrometer 10 from the gas 26 flowing through the sample cell 20 with known results. The models will be built from a variety of different sources. Parts of the models are created by correlating output values from a GC with the spectrum of the same gas. In addition to the GC correlation, one may mix gasses of known composition and record their respective spectrums using the spectrograph. Pressure and temperature will be recorded to account for their effects. Any offsets or adjustments required will be included in the calibration models. All of this information is compiled and used as a reference to compare the information coming from the on-line monitor. The calibration set will allow one to derive the sample's energy content in both dry and saturated states, compressibility, hydrocarbon dew point, moisture content, specific gravity, Wobbe index and other like information.

Embodiments of the present invention have the ability to transmit the data back to a gathering location to keep a recorded history of values. The transmission can be wireless or via hard wire. Some configurations may perform data processing on-board while others will send raw data that will be processed by another computer that has the chemometric models and analytical software.

Power may be provided by a rechargeable battery source that can be replenished by solar power, generator, or hard line electricity. The direct current of the battery source may run through an inverter to achieve alternating current of a 120 or 240 volts @ 60 hertz. Alternatively, another embodiment may employ DC to directly power all components and modules. This may be used to power the spectrometer, light source 12, the on-board computing module, pressure transducers, temperature sensing modules, any heating elements, data transmitting equipment, and the valve control manifold for the sampling system. This reduces the required infrastructure needed to support the sensors in the field.

Figure 2:
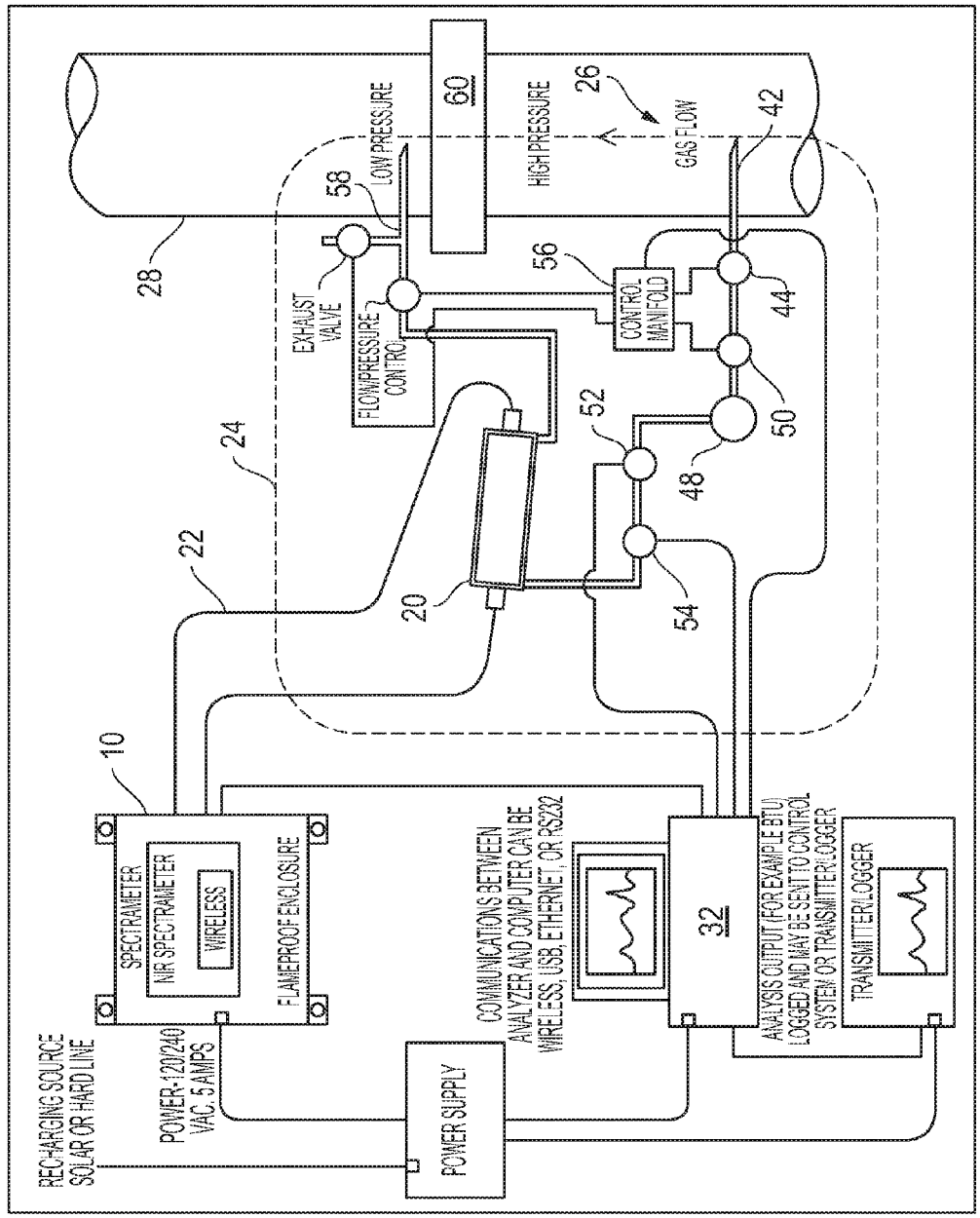
FIG. 2 provides a sample system used in combination with the spectrometer of FIG. 1 in accordance with an embodiment of the present invention.

Sampling system 24 as shown in FIG. 2 will include sample probe 42 to extract gas 26 from the transmission line 28, a shut off valve 44, a switching valve, a filter 48, a flow controller or regulator 50, a pressure transducer 52, a temperature probe 54, an optical cell 20 coupled with fiber optic cables 22, a heater operable to heat the sampled gas, another flow controller or regulator 56, and a connection 58 to reintroduce the sample gas or exhaust the sampled gas. The sample system will preferably operate across a constriction point 60 in transmission line 28 in order to create a pressure differential to flow gas though the sample loop. Due to the fact that optical measurement is non-invasive, the sample may be reintroduced into the gas transmission line 28 but may be exhausted if the site set-up is not conducive to reintroduction. A small pump may be used for reintroduction if no pressure delta can readily be established. Sample loop valves may be actuated by a switching manifold controlled by the on-board electronics. The pressure and temperature sensors provide data signals to the on-board electronics to be included in the data log for each respective spectral recording. The signals may be 4-20 ma analog signals or 0-5 volt DC signals. Pressure through the sampling system may be about 100 psi, although other pressures both higher and lower are contemplated. The gas cell will be at an angle such that any liquids that may condense can flow out and not build up in the cell. These spectrographs may be repeated on the order of every 20 milliseconds or as specified by data management requirements. In some embodiments but not all, the spectrometer and electronics may be housed in an enclosure that is explosion proof and rated for Div. 1 Class 1 environments.

Figure 3:
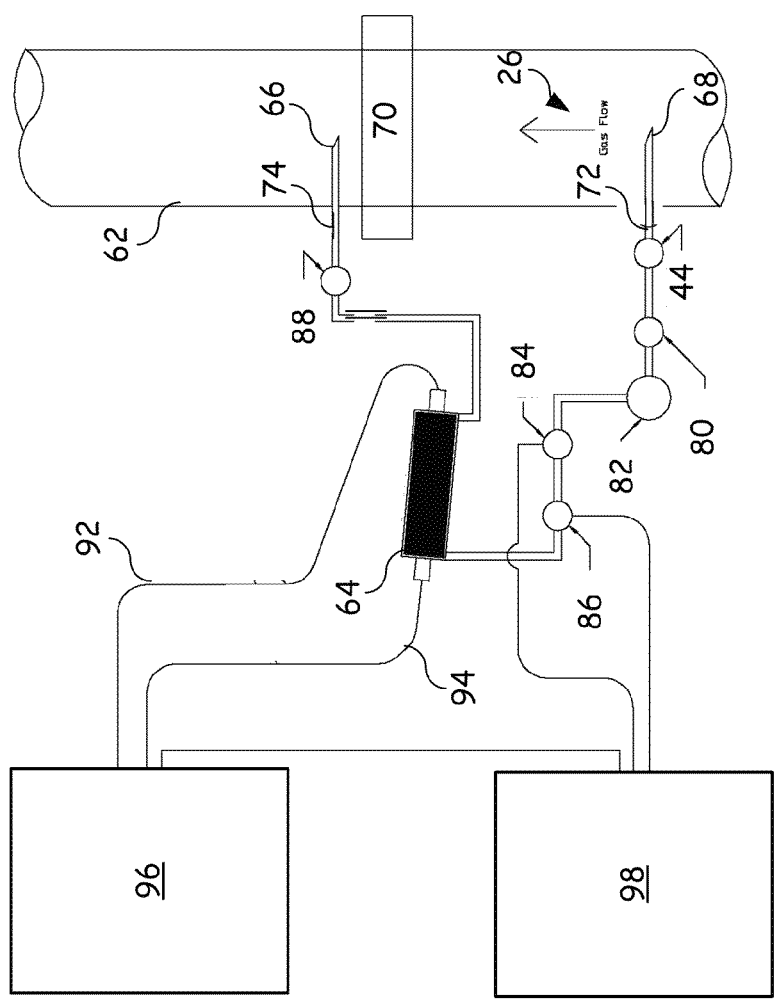
FIG. 3 depicts a another embodiment in accordance with the present invention wherein a remote optical sensor is used coupled to a gas collection or transmission system in accordance with an embodiment of the present invention.

FIG. 3 shows another embodiment of the present invention wherein a remote optical sensor is used to couple to a gas collection and/or transmission system. Here gas flow 26 within a piping infrastructure 62 has a series of physical and chemical properties associated with the gas. As shown here optical cell 64 is placed between a low pressure tap 66 and high pressure tap 68 through which sample gas flows. Differential pressure drives flow through optical cell 64 is provided by a restrictor or volume metering device 70. This embodiment and that as shown in FIG. 2, show how optical cell 64 may be placed in sample lines which may have been previously used to take gas samples which would have been processed using gas chromatography. High pressure sample line 72 and low pressure sample line 74 may be isolated from the gas flow 26 using shutoff valves. A flow pressure controller 80 is used to control the amount of flow to optical cell 64.

Additionally gas flow may be filtered using a gas filter 82. Physical parameters associated with the gas such as but not limited to pressure and temperature may be measured using pressure sensor 84 and temperature sensor 86 respectively. Gas flow through optical cell 64 is returned through the low pressure line 66 which may further include a low pressure controller 88 wherein flow pressure controller 80 and 88 may be controlled using a control manifold.

Fiber optic cables 92 and 94 may be used to couple optical cell 64 to spectrometer 96. As described previously this spectrometer may be a NIR spectrometer in order to more efficiently deliver light to and from optical cell 64.

A computer or processing module 98 may be used to take the outputs from the spectrometer 96 and other sensors such as temperature sensor 86 and pressure sensor 84 in order to determine the energy content associated with the gas flow 26.

Figure 4:
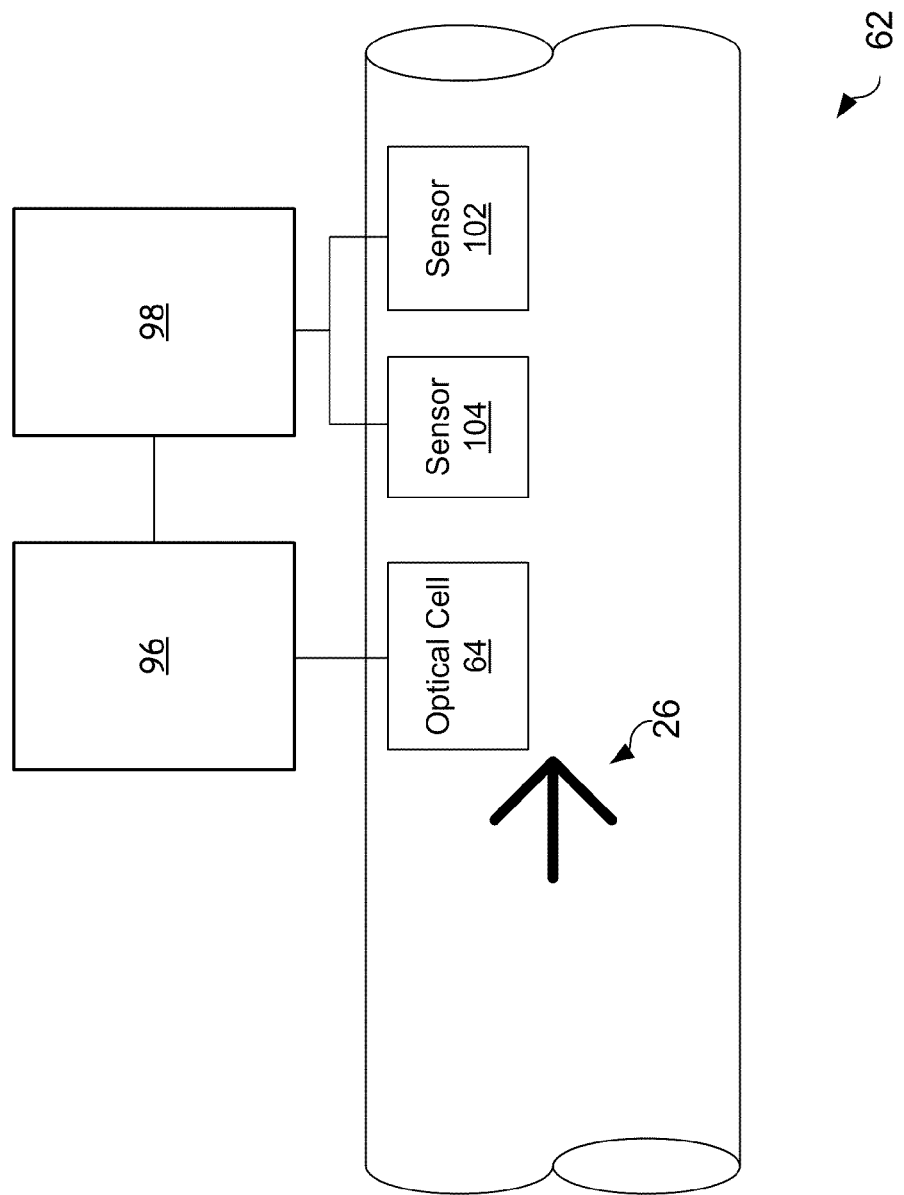
FIG. 4 depicts another embodiment of the present invention wherein the optical cell is located within the gas flow in accordance with an embodiment of the present invention in order to eliminate many of the complexities associated with an external sample system.

FIG. 4 depicts a second embodiment wherein the optical cell 64 is located within gas flow 26. This eliminates much of the need for low pressure lines and high pressure lines. In addition to optical cell 64 other sensors such as pressure sensor 102 and temperature sensor 104 may be located within gas flow 26 as well. As shown previously, the optical cell may be optically coupled using fiber optics or other like materials to spectrometer 96. Sensors 102, 104 as well as spectrometer 96 may all be communicatively coupled to a processing module 98 which may then determine the chemical composition associated with gas flow. These individual modules may be coupled wirelessly or via wired connections.

Spectrographs use chemometeric models and other analytical techniques to determine the composition of the gas. The data models are used to compare the spectrums being gathered by the spectrometer from the gas flowing through the sample cell with known results. Pressure and temperature will be recorded to account for their effects. Any offsets or adjustments required will be included in the calibration models. All of this information is compiled and used as a reference to compare the information coming from the on-line monitor. The calibration set allows one to derive the sample's energy content in both dry and saturated states, compressibility, hydrocarbon dew point, specific gravity, moisture content and Wobbe index. The models may reside on each individual installation or on a central server. The units with all the analytical capabilities on-board will send compiled data while other units may transmit raw telemetry that will be analyzed by a central server. The server will have the chemometric models and other analytical software necessary to complete the analysis.

The efficiencies enabled by a distributed network spectrographs that provide on-line data create a new battery of decision making matrices with many different permutations. Some examples include:

1. Contract Adherence: Natural Gas suppliers and purchasing agents agree to certain quality stipulations of the gas that is being transacted. The spectrometers will be able to immediately determine if certain properties are out of contractual specifications. Examples of properties monitored are hydrocarbon dew point, moisture content and impurities. Chemical composition may change and alter the hydrocarbon dew point of the gas which may result in equipment damage and hydrocarbon drop out (condensation) down the line. The hydrocarbon condensation will result in lost energy in the transmission system and act as a catalyst for corrosion. Some examples of impurities are carbon dioxide, nitrogen, water, and hydrogen sulfide. This information may invoke a certain discounted price or penalty while the gas remains out of a premium price quality standard.

2. Process Optimization: Gas processing plants run different process configurations based on current market conditions and the attributes of the raw material feeds. Real-time data provided by the spectrometers will enable processing plants to quickly react to changes in the composition of the gas entering the plant. This will allow these processing facilities to optimize the processes running and operate at a much greater efficiency than is currently possible. Similarly, in field processing equipment such as $H_2S$ scrubber filters may be selectively placed on service or configured based on the quality of the gas.

Large natural gas consumers such as electrical utilities and cement producers may adjust the burners based on changes in composition in order to optimize their processes and ensure the quality of the products they produce. As little as a 50 BTU fluctuation will have a profound impact of the performance of a burner.

3. Field Production Efficiency/Reservoir Management: As oil and gas producing fields age, the wells need maintenance and service. The streaming data from the spectrometers will inform personnel when a well is losing productive efficiency or if another problem exists. A decision can be made on what kind of service a well is going to need or if a new zone needs to be perforated. Wells may be taken off-line or brought back on-line based on the quality of the gas coming out of the well at the time and the current market price for such gas.

4. Historical Trending and Present Value Calculations: The information from the spectrographs can be stored on a data server where the data can be processed for historical trending. The trends can be used to characterize wells and production fields for valuation purposes and production schedules. The information may also be used to determine if drilling more wells is economically viable.

5. Payment Terms: Data servers can store the information during payment cycles. The data can then be compiled into a report where the value of the payment can be determined. The reports may be printed and mailed or distributed electronically. The information can also be used to adhere to any sort of regulatory filings required. Clients will have the ability to access a reporting server via the internet.

Figure 5:
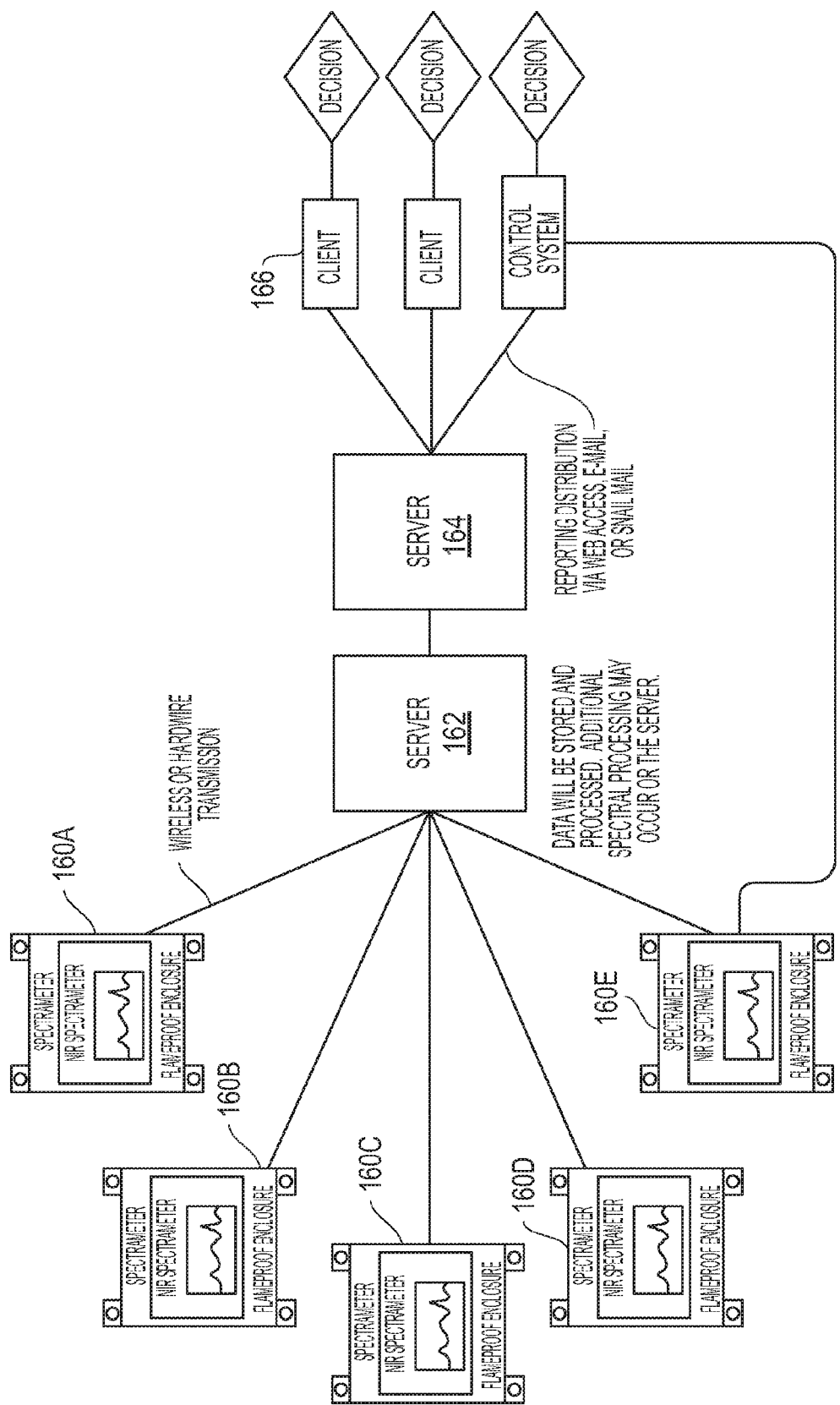
FIG. 5 shows a distributed network in accordance with an embodiment of the present invention where the sensor systems may be located at various nodes within the transmission infrastructure and collection infrastructure.

The systems as shown in the previous FIGs. may be used to determine the chemical composition or energy content of gas flow 10 in near real time at discreet locations within a gas collection and transmission infrastructure. FIG. 5 shows a distributed network where the sensor systems 160A through 160E may be located at various nodes within the transmission infrastructure or at various collection points within the collection infrastructure. For example individual wells may have these data collection systems attached to the output attached placed such that the energy content and chemical composition associated with the output of an individual well may be determined. This is important as it may identify the production capabilities and qualities of an individual well or reservoir. This information may also be used to determine when a need exists to perform maintenance or repair tasks associated with a well in order to improve the quality and content of the natural gas produced therein.

Remote sensors system 160A through 160E may be coupled to a data gathering server 162. This server will allow data to be stored and processed. Additionally should a need exist to off load spectral processing of data gathered by the spectrometer sensing systems remotely located within the gas collection transmission infrastructure, additional processing capabilities at the data gathering server 162 may be used to determine the chemical composition and energy content of the natural gas. The reporting server 164 having access to the data gathering server may then use the data or provide the data to client applications 166 from the individual collection points to determine the need for maintenance, the pricing structure based on the quality and content of the natural gas, or other like needs. For example natural gases delivered to a processing refinery may be delivered with real time chemical composition and energy content information such that the individual processing modules within the refinery may be reconfigured based on the actual raw material feed composition as opposed to standard process practices which less frequently sample the gases and can result in non-optimal configurations at manufacturing facilities when processing the natural gas. In another embodiment the information delivered to the client may be used to determine in real time the energy content and associated price associated with the natural gas delivered to an end user such as a utility.

Figure 6:
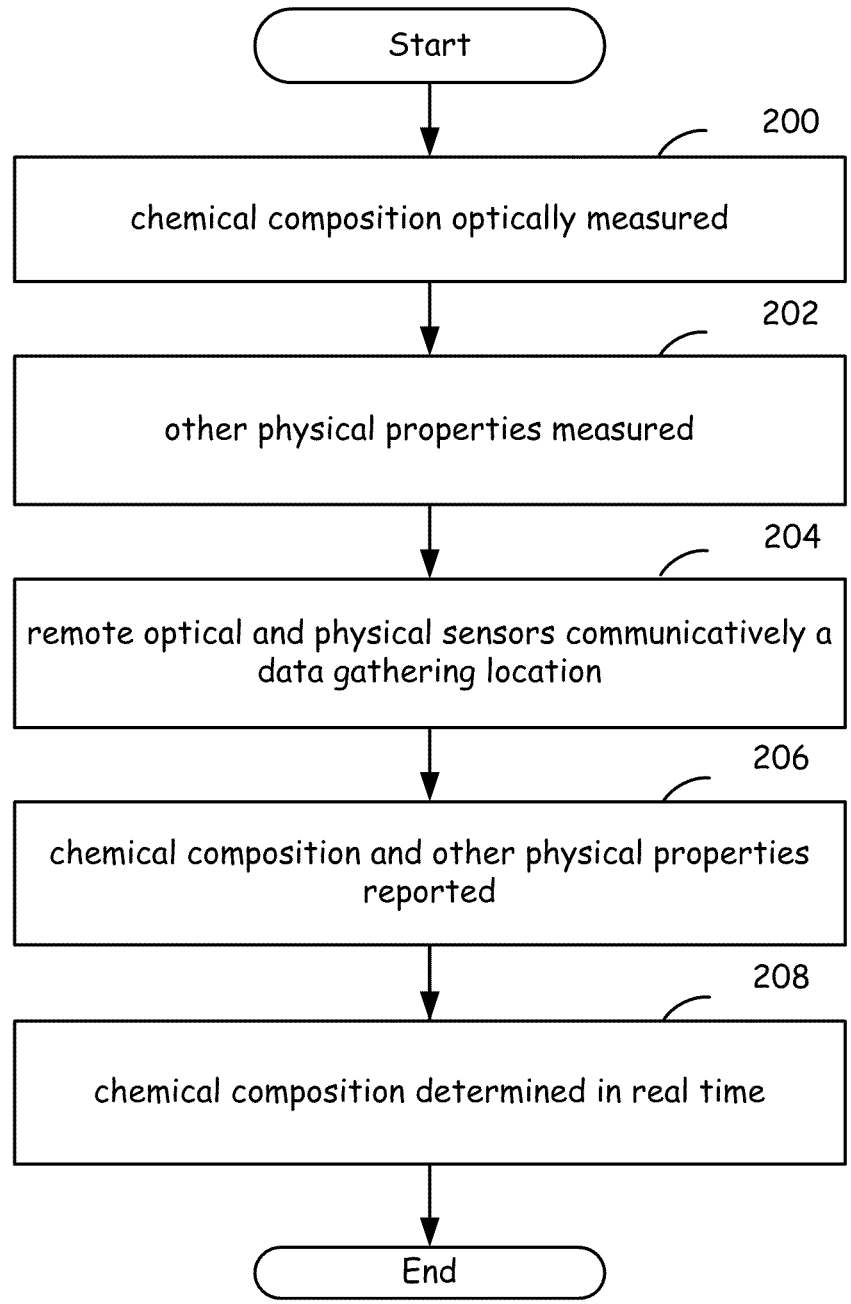
FIG. 6 provides a logic flow diagram in accordance with an embodiment of the present invention that describes how the chemical properties of a gas may be determined using remote optical sensors.

FIG. 6 provides logic flow diagram and a method to optically determine the chemical composition of the natural gas in accordance with embodiments in the present invention. In Step 200 the chemical composition of the natural gas may be optically measured using remote optical sensors within a gas collection and transmission infrastructure. In Step 202 other physical properties associated with the natural gas may be measured. These properties may include temperature and pressure but are not so limited. The chemical composition may be based on the spectrographic analysis performed using remote optical sensors. This information is combined with information such as pressure and temperature to determine overall energy content associated with the gas. The remote optical and physical sensors may be communicatively coupled in Step 204 to a data gathering location. In Step 206 the chemical composition of the natural gas as well as the other physical properties may be reported to a computer processor which may be located locally or at the data gathering location. In Step 208 the chemical composition associated with bulk quantities of the natural gas may then be determined in real time. For example using spectrographic analysis it may be possible to perform samples as often as every 20 milliseconds. This differs greatly from current practices wherein samples are taken perhaps on a monthly or quarterly basis. This analysis allows natural gas to be priced using real time chemical compositions associated with bulk quantities of the gas within the gas collection and transmission infrastructure. Another embodiment allows the downstream user to access this information in order to reconfigure manufacturing processes based on real time chemical compositions of the natural gas to be delivered. Yet another embodiment allows this methodology to be applied in the field or gathering location wherein scrubbing and filtering equipment may be placed on or off service based on the quality and contaminants contained within the gas being supplied to and delivered from the gathering location.

Figure 7A:
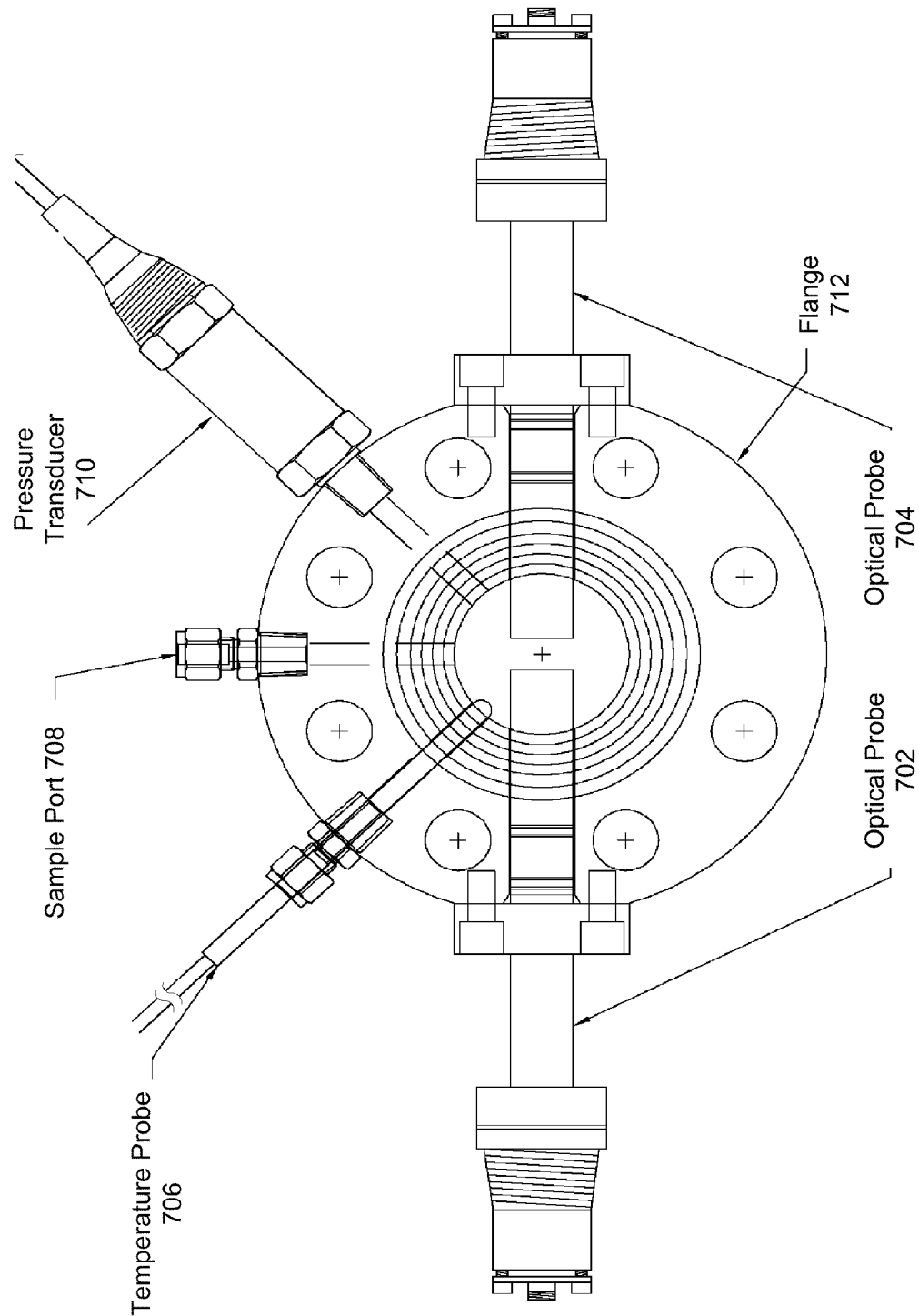
FIGS. 7A-7D picture embodiments of the present invention operable to measure the chemical composition of a gas within a pipeline.

FIG. 7A pictures one embodiment of the present invention wherein a Flange Type Device 700 is provided to measure the chemical composition of a gas within a pipeline. As shown here Chemical Composition Analyzer 700 includes Optical Probes 702 and 704, Temperature Probe 706, a Sample Port 708, and a Pressure Transducer 710. These probes and ports are incorporated within an ANSI Compatible Flange 712. The optical probes allow spectroscopic measurements to be taken and combined with the results of the Pressure Transducer 710 and Temperature Transducer 706 in order to yield information about the quality and quantity of hydrocarbons or other gasses within the transmission pipe in which Flange Chemical Composition Analyzer 700 is installed.

Figure 7B:
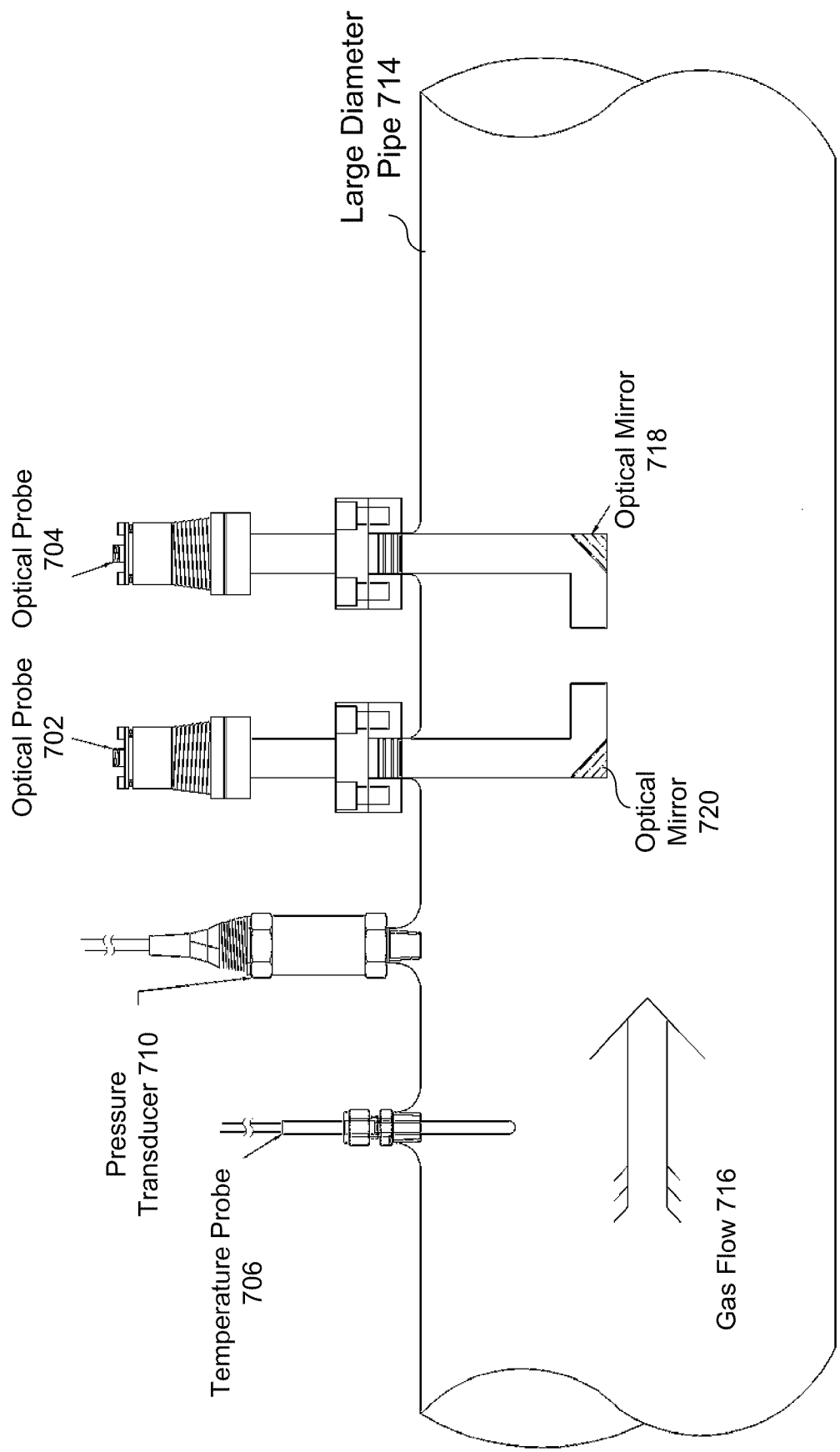

FIG. 7B pictures one embodiment of the present invention wherein individual probes are introduced to a large diameter pipe 720 to measure the chemical composition of a gas within a pipeline. As shown here Chemical Composition Analyzer 700 includes Optical Probes 702 and 704, Temperature Probe 706, a Sample Port 708, and a Pressure Transducer 710. These probes and ports are incorporated within an ANSI large diameter pipe 720. The optical probes allow spectroscopic measurements to be taken and combined with the results of the Pressure Transducer 710 and Temperature Transducer 706 in order to yield information about the quality and quantity of hydrocarbons or other gasses within the transmission pipe in which Composition Analyzer 700 is installed.

Figure 7C:
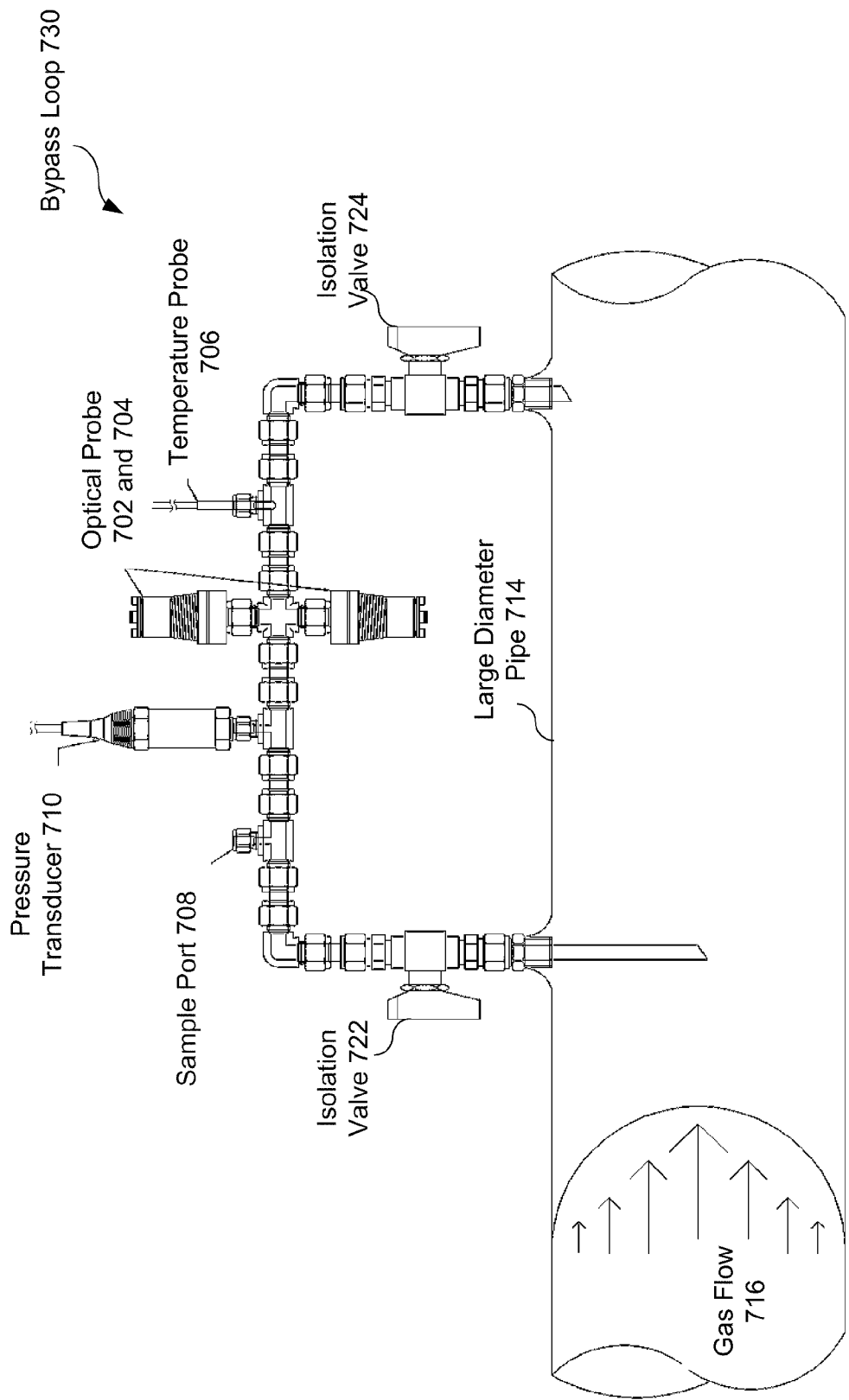

FIG. 7C pictures one embodiment of the present invention wherein individual probes are introduced to a large diameter pipe 720 to measure the chemical composition of a gas within a pipeline using a bypass loop 730. As shown here Chemical Composition Analyzer 700 comprises a bypass loop 730 that includes isolation valves 722 and 724, Optical Probes 702 and 704, Temperature Probe 706, a Sample Port 708, and a Pressure Transducer 710. The optical probes allow spectroscopic measurements to be taken and combined with the results of the Pressure Transducer 710 and Temperature Transducer 706 in order to yield information about the quality and quantity of hydrocarbons or other gasses within the transmission pipe in which Composition Analyzer 700 is installed.

Figure 7D:
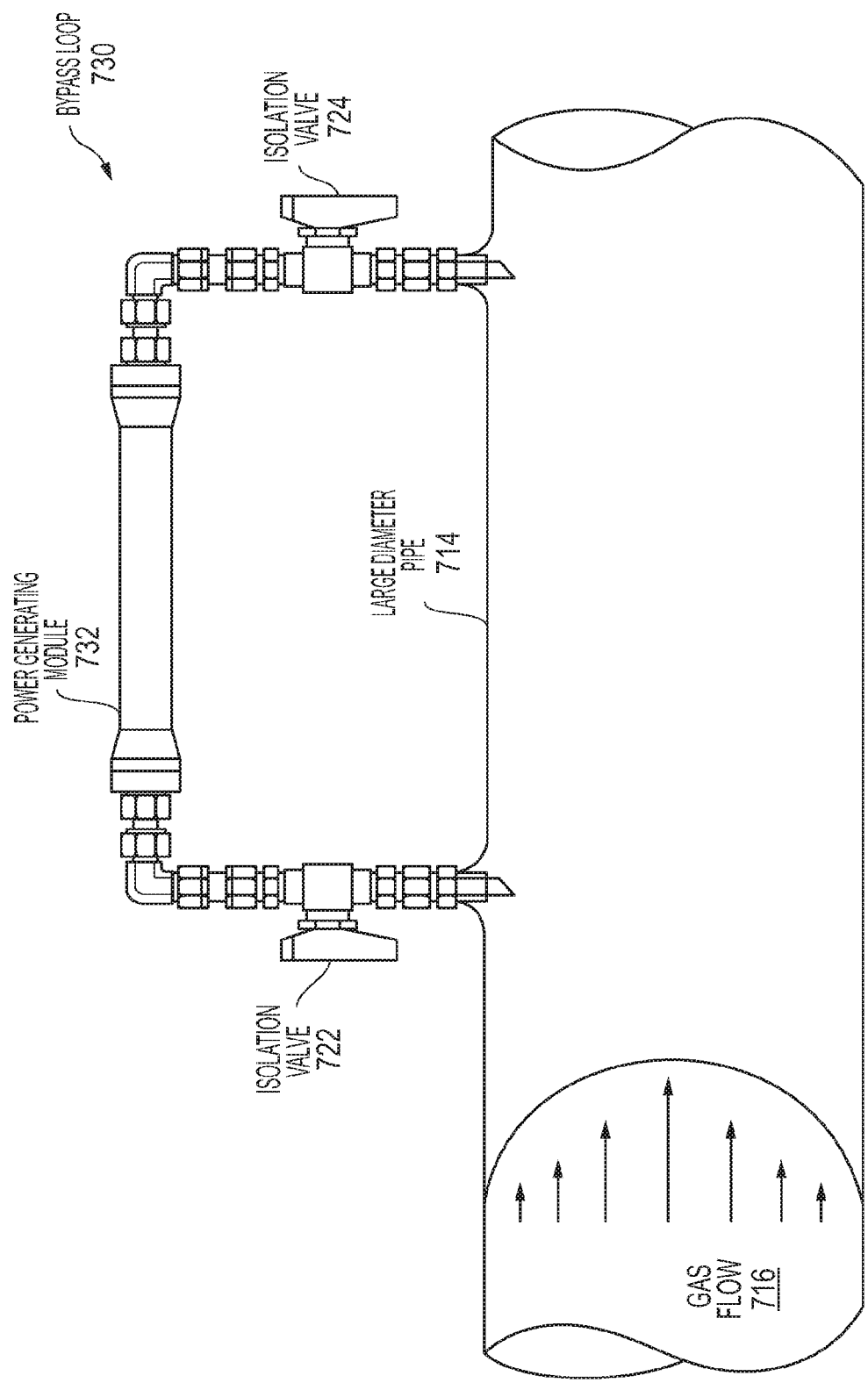

The Chemical Composition analyzer 700 may be powered from a power generating device operable to extract energy from the gas flow 716. This may be extracted from the kinetic energy of the gas flow or directly from the gas itself. FIG. 7D provides one example where power generating module 732 (i.e. a turbine) is used to extract energy from the gas flow. This may be in a bypass line 730 or within the pipe 714 itself. A squirrel cage type stator and armature may be used to eliminate the need for electrical penetrations of the pipe.

Figure 8:
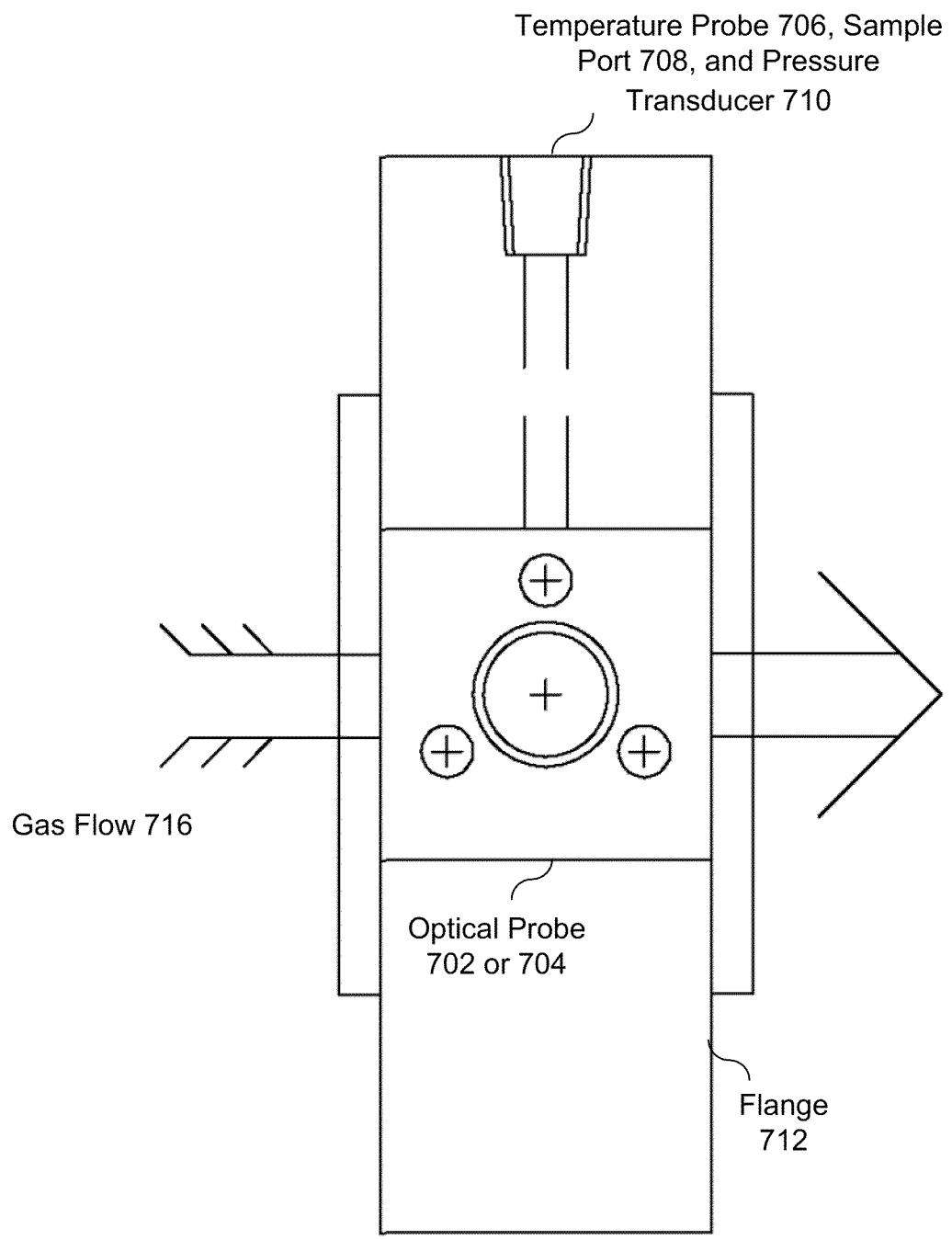
FIG. 8 provides a side view of Gas Flange Chemical Composition Analyzer of FIG. 7A.

FIG. 8 provides a side view of Chemical Composition Analyzer 700 in the form of a flange device. As is shown here Gas Flow 716 flows within the Flange Device 712. Here one Optical Probe 702 as well as an additional port such as Sample Port 708 is depicted.

The process provided by embodiments of the present invention may record a spectral intensity profile of an empty sample cell with only $N_2$ or ambient air (no natural gas present) in the optical path, call it a reference scan (Ir), store this scan. The Near-Infrared band of the electromagnetic spectrum is used here. Specifically from about 1300 nm-2000 nm.

Then a spectral intensity profile with the same sample cell filled with flowing gas, call it a sample scan (Is) may be recorded. Spectra are taken by combining the light from multiple laser sources into a single scanning beam.

Figure 9:
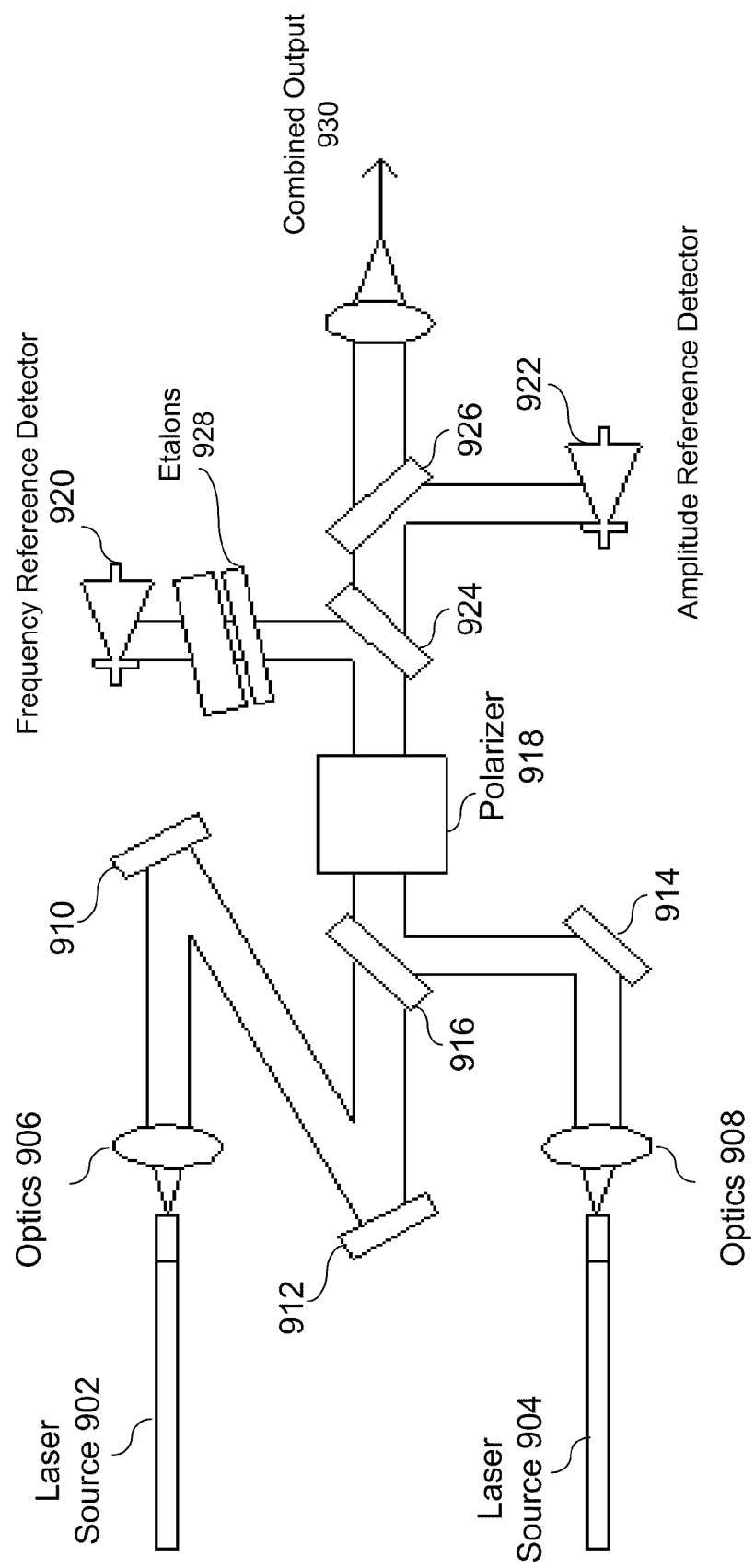
FIG. 9 provides a block diagram of a laser source 900 for an analysis system in accordance with embodiments of the present invention.

FIG. 9 provides a block diagram of a laser source 900 for an analysis system in accordance with embodiments of the present invention. Laser source 900 may include multiple different laser sources, such as laser source 902 and 904, to detect different analytes of interest. For example one Laser source 902 may be able detect the combustible components methane, ethane, etc. . . . while Laser source 904 may be used to determine $H_2S$ concentrations, yet another laser source (not shown) may be used for the non-combustible components such as $H_2O$, $CO_2$, etc. The light from the lasers 902 and 904 is sent through optics 906 and 908 respectively. Optics 906 and 908 may be single focusing lens for each laser (lens to focus diverging light coming out of fiber) and combined into a single beam using mirrors 910 912, 914 and 916. The beam is then polarized with polarizer 918. A small percentage of the beam is ported off to 2 different detectors 920 and 922 using beam splitters 924 and 926. The output from detectors 920 and 922 is sent back to the analog electronics board in order to correct for any deviation in the light sources over time. The portion that is ported off to manage the frequency of the light is sent through multiple Etalons (optical filters) 928 to filter the light at specific wavelengths. These specific peaks are then used to calibrate the frequency of the lasers. The portion that is sent to the Amplitude reference detector is used to manage the power output of the lasers. Additional laser sources could be combined in a similar manner.

Figure 10:
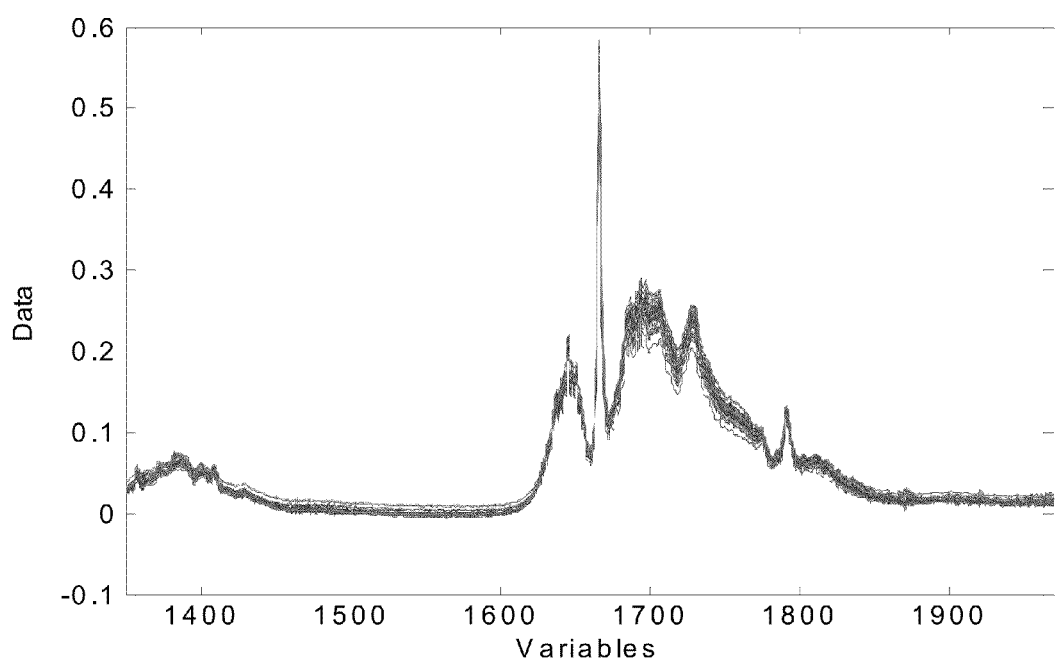
FIG. 10 shows an example of an absorption spectra in the near infrared range.
Figure 11A:
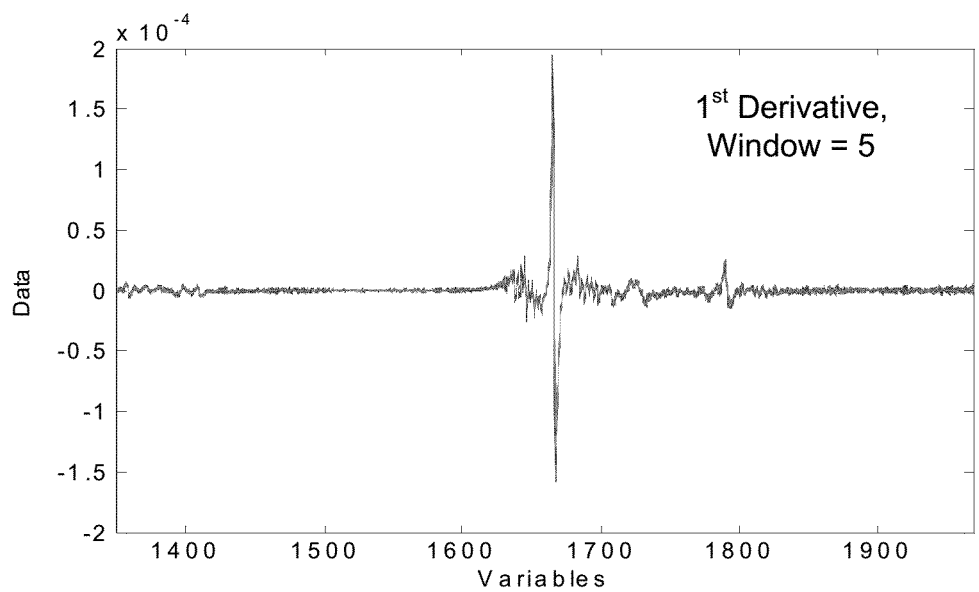
FIGS. 11A-D provide examples of the calculates 1st derivative of the absorbance spectrum of FIG. 10 in accordance with embodiments of the present invention.
Figure 11B:
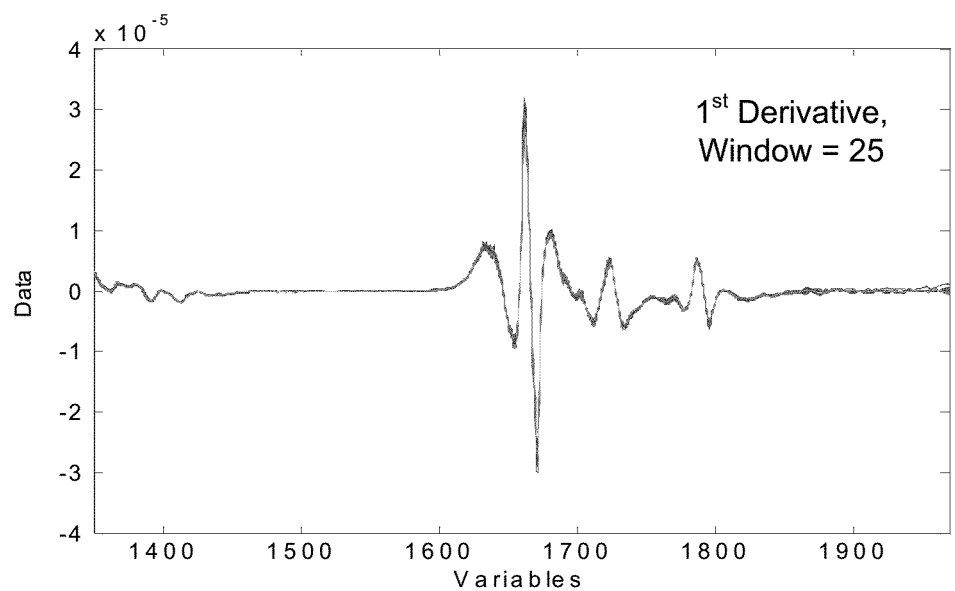
Figure 11C:
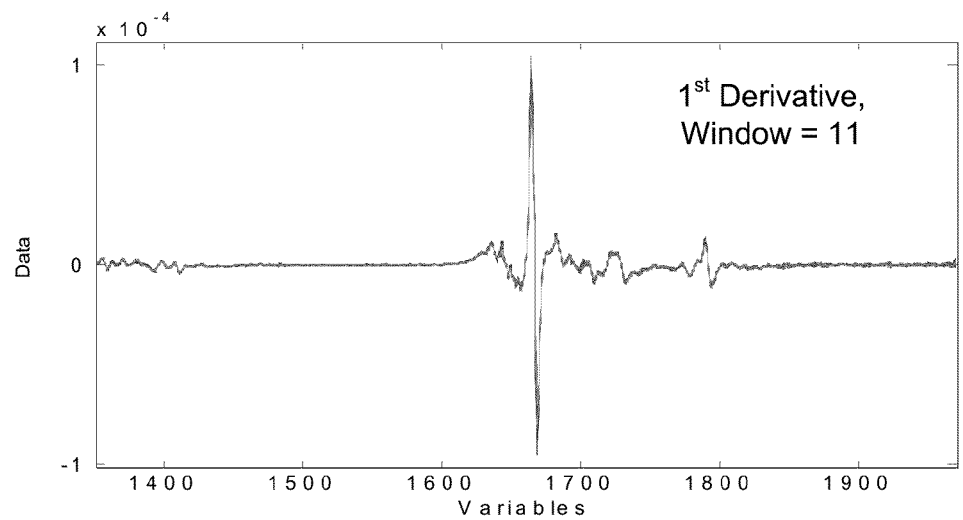
Figure 11D:
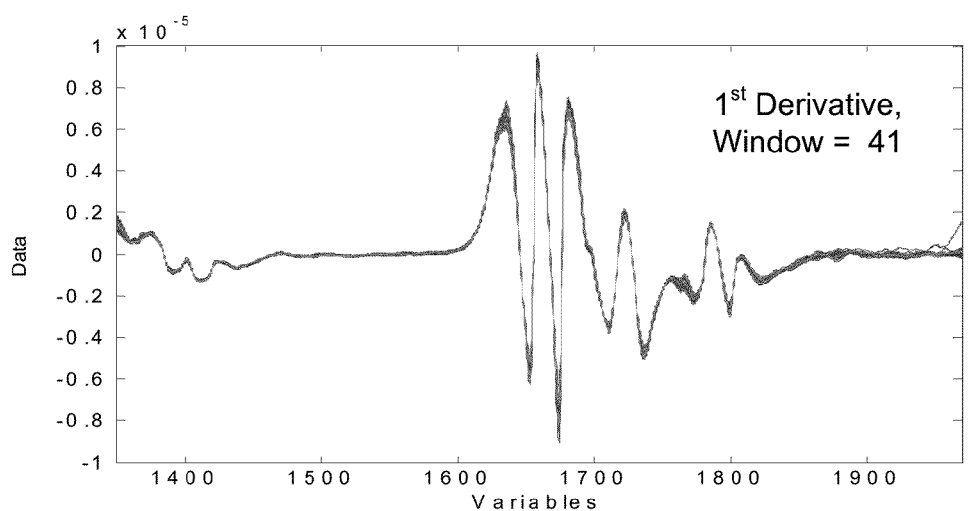

The calibrated beam is then sent out to the sample probes, as shown in FIGS. 7A-C and 8, and an absorption spectra is taken from the gas and stored in a database. With the absorption spectra, the sample temperature and pressure is recorded. The absorbance spectrum as $A=-\log(Is/Ir)$. FIG. 10 provides an example of collected absorbance spectra.

FIGS. 11A-D provide examples of the calculates 1st derivative of the absorbance spectrum of FIG. 10 in accordance with embodiments of the present invention, using the Savitsky-Golay algorithm, with polynomial order=X, and window width of =W. Specifically, FIGS. 11A-D provide examples of polynomial=2 at different window widths.

The process next involves dividing the 1st derivative spectrum by the pressure (in PSI) for normalization. One or more calibration models are then applied to the normalized 1st derivative spectrum to calculate energy content, $H_2S$, $H_2O$, $CO_2$ concentrations, other gas properties, such as compressibility, density or the presence of multi-phase material, and "spectral abnormality" diagnostics. if the spectral abnormality diagnostics are favorable, transmit results (BTU, other property values) to the appropriate location; if they are not favorable, prevent any predicted results (BTU, etc.) from being used for control (or other) purposes.

Figure 12:
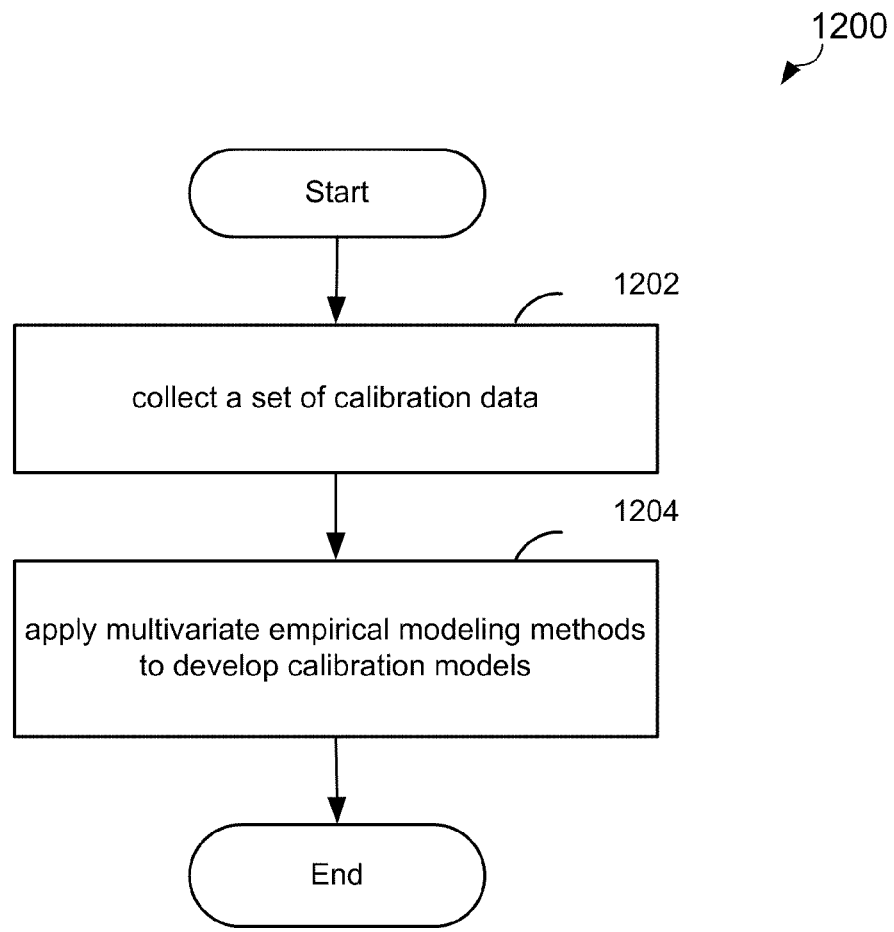
FIG. 12 provides a logic flow diagram describing how the calibration models are developed in accordance with embodiments of the present invention.

FIG. 12 provides a logic flow diagram describing how the calibration models are developed in accordance with embodiments of the present invention. Calibration development process 1200 begins with step 1202. Step 1202 collects a set of calibration data, to be used to develop the model. This calibration dataset must have matching NIR spectral data (X) and property data (Y). Such data can be collected in several ways, including: (1) injecting gas samples of known properties into the sample cell, and recording their spectrum as described above; and (2) recording the spectrum of an on-line flowing gas sample, accompanied by subsequent capture and laboratory analysis of an extracted gas sample (where the sample was collected at the same time and same location where the spectrum was collected). Step 1204 applies multivariate empirical modeling methods to develop calibration models, given the calibration data collected in 1202. This model development work can involve one or more of the following elements: (1) Use of Principal Components Analysis (PCA) and Partial Least Squares (PLS) Regression to "explore" the calibration data, to uncover optimal modeling strategies and to detect potential outliers in the calibration data set; (2) If any outliers (samples or spectral variables) are detected in the calibration data, exclude them from being used to build the models; (3) Use of Partial Least Squares (PLS) Regression, to construct predictive calibration models from the calibration data; this method generates a series of regression coefficients (b) which, when multiplied with the absorbance values (A) of an unknown gas sample's spectrum, will yield the property of interest; (4) Use of Genetic Algorithms (GA) to select subsets of the spectral response variables to use in the predictive models this is done to make the PLS models more robust with respect to known interfering effects in the spectra; (5) use of PCA to generate an "outlier model", which can be run on-line to assess whether a field-collected spectrum is abnormal, with respect to the spectra that were used to develop the models; this model can be used to generate "spectral abnormality" diagnostics, which can be used as described above.

Figure 13A:
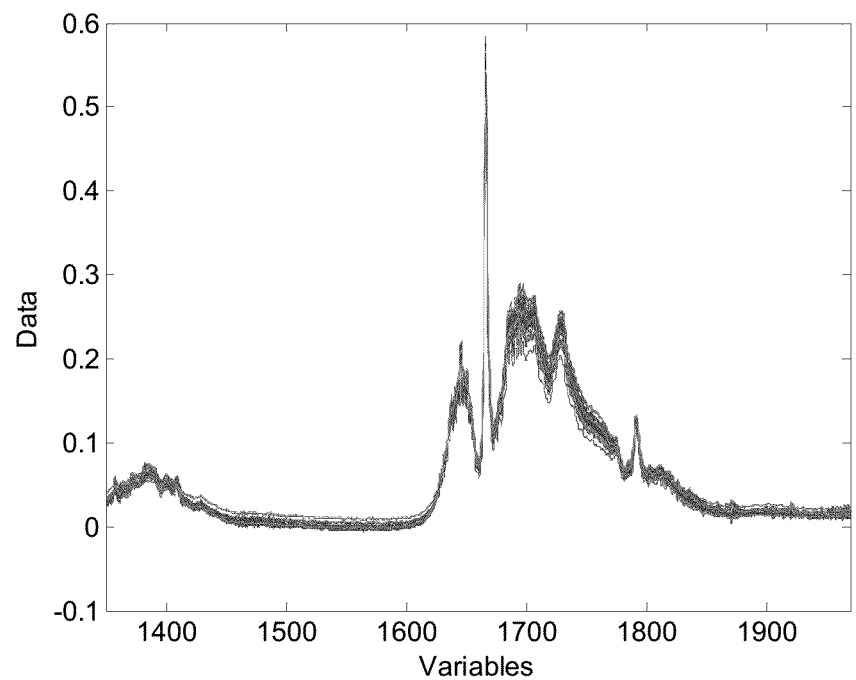
FIGS. 13A and 13B depict a raw spectra and $1^{st}$ derivative associated with the optical measurements taken in accordance with embodiments of the present invention.
Figure 13B:
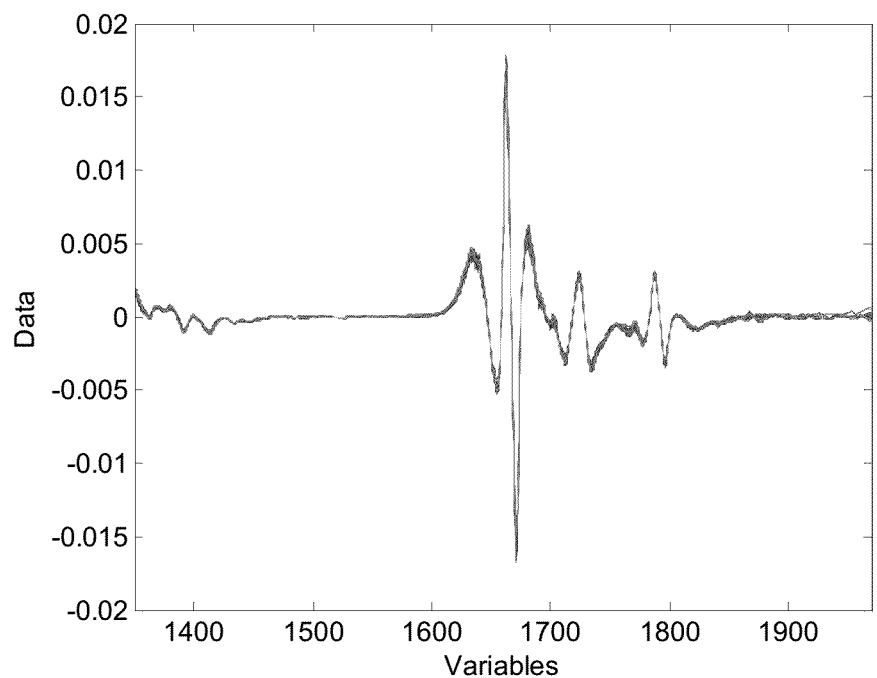

FIGS. 13A and 13B depict another raw spectra and $1^{st}$ derivative associated with the optical measurements taken in accordance with embodiments of the present invention.

Figure 14:
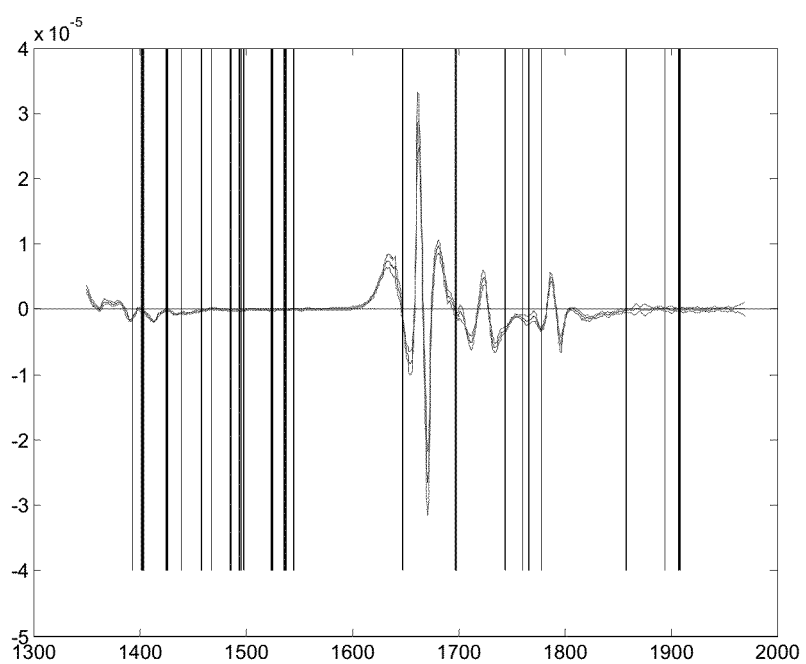
FIG. 14 depict Near Infrared spectrographic analysis associated with the optical measurements taken in accordance with embodiments of the present invention.

FIG. 14 depicts Near Infrared spectrographic analysis associated with the optical measurements taken in accordance with embodiments of the present invention where wavelength subset selection is performed to identify component gases and energy values. Embodiments of the present invention provide improved analysis techniques over existing techniques by processing collected spectral information by identifying wavelength sub-sets of interest that may be associated with various chemical components and by using the 1st derivative of the spectrograph to identify chemical components within the spectrograph.

Figure 15:
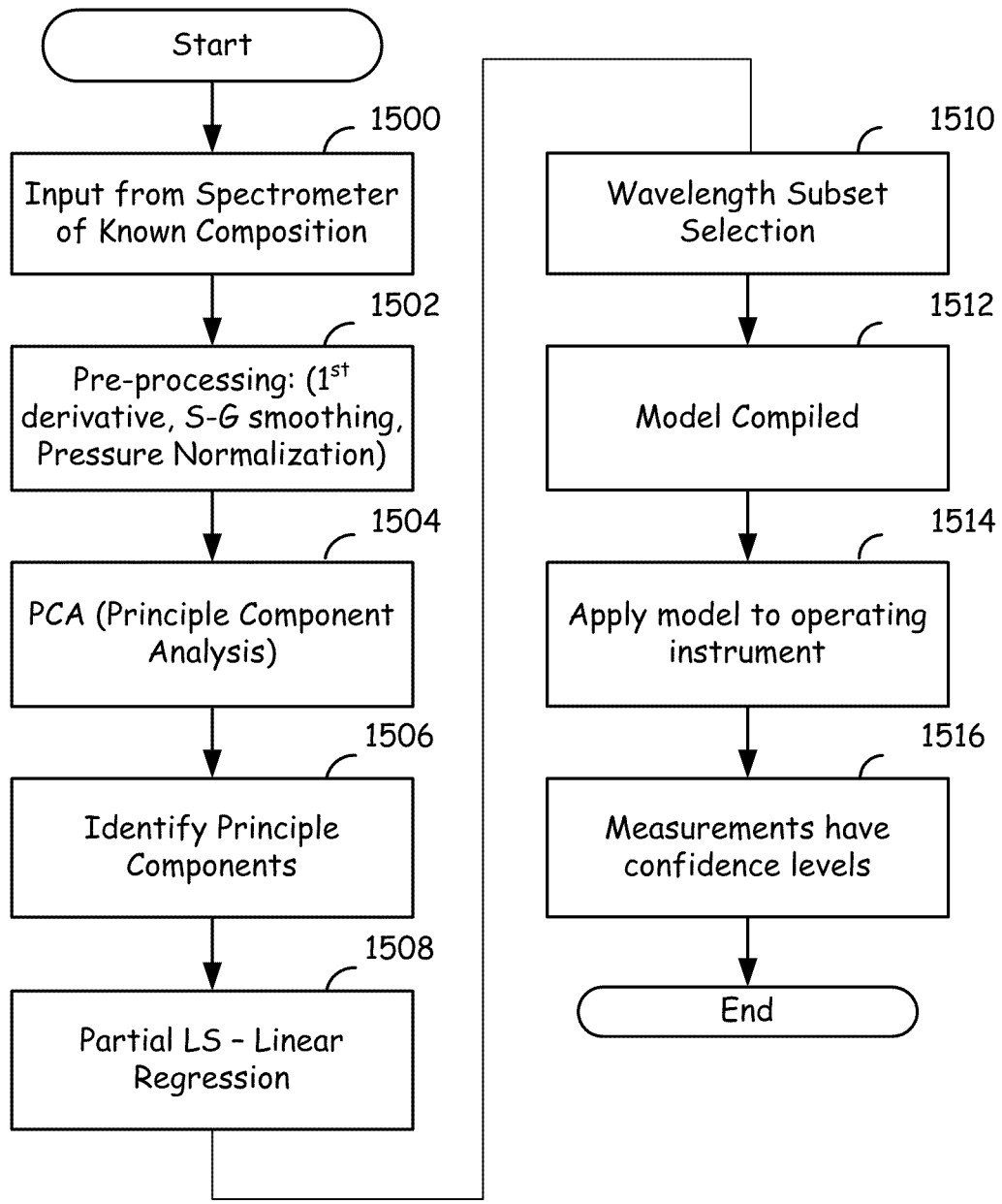
FIG. 15 provides a logic flow diagram of a linear regression multi variant process used to determine the chemical composition of a measured gas.

FIG. 15 provides a logic flow diagram of a linear regression multi variant process used to determine the chemical composition of a measured gas.

In another embodiment the present invention does not need to be installed in a gas stream but rather may be installed as a leak detection unit within a refinery gas processing facility wellhead or any other place where toxic chemicals may be expected. This allows not only detection of chemical components within the atmosphere but the concentration of those components as well. This process may begin in step 1500 where input from a Spectrometer of a gas having a Known Composition is provided.

Embodiments of the present invention may also provide processing spectrographic information generated by true on-line instrument that optically analyzes Natural Gas, to include the process of liquification and regasification natural gas, in an attempt to determine the chemical composition or other physical attributes of the material. Properties of interest may include but are not limited to: energy content (expressed in British Thermal Units; BTU), dew point (both Hydrocarbon and Water), water content, Hydrogen Sulfide content, Carbon Dioxide content, flow rate in an active pipeline, compressibility, specific gravity, and Wobbe index. The Near Infrared band of the electromagnetic spectrum is used to derive the information; specifically between the 1300 nm to 2500 nm range. Embodiments of the present invention may focus on the 1350 nm to 1970 nm range.

This technology can replace multiple analytical devices because of the ability to simultaneously detect many different properties and chemical species. Embodiments of the present invention also have the ability to make measurements at operating temperatures and pressures without sample extraction or conditioning. This provides an environmentally friendly device that can instantly stream valuable data about process lines to the operators who need it to make decisions.

Hydrogen Sulfide ($H_2S$) and energy content of natural gas, including liquefied natural gas, is of particular interest. $H_2S$ is a toxic chemical that needs to be treated as effectively as possible to maintain safe operating conditions. Energy content is what drives the value of Natural Gas. Therefore, an on-line system that can instantly make measurements in a process line is an extremely valuable tool that can keep a safe working environment and create an efficient marketplace by providing true valuation of assets.

Recent advances in the application of mathematical principles to spectrographic information have created the ability to derive chemical and physical properties of an analyte. Specifically, pre-processing of the spectra and dividing the information into specific windows that are analyzed to reveal the chemical composition of a natural gas stream.

Pre-processing, as shown in step 1502, of the spectra may involve, but is not limited to, taking the first derivate of the absorbance spectra and applying a simple pressure normalization that involves multiplying by 1/P. This randomizes the baseline offset effect and provides for better separation by sample temperature.

Once the pre-processing is complete, Principle Component Analysis ("PCA") is used in step 1504 to identify covariance trends in the multivariate data for exploratory purposes. Principle Components ("PCs") are identified in step 1506 that account for the variability in the spectra taken from different samples. These components are then used to help guide the most efficient methods to build predictive models. The PCs can represent things such as: changes in chemical composition, effects of different pressure conditions, and changes in temperature to name a few.

After the PCA analysis is done, Partial Least Squares ("PLS") is applied to the spectra in step 1508. PLS is similar to PCA but adds the ability to include linear regression. This ability facilitates the creation of predictive models that can determine attributes of an analyte. These attributes include but are not limited to: BTU value, mole percent of a chosen chemical species, specific gravity, dew point, water content, and compressibility.

In order to simplify model creation in step 1512 specific subsets of the spectra are selected that demonstrate strong correlations to the property, or properties, of interest in step 1510. This model may then be applied to an operating instrument in step 1514 to ensure a level of confidence associated with the measurements.

Near Infrared spectrographic analysis is a non-invasive optical measurement that has no emissions. There is no need for calibration gases or carrier gases to perform measurements as with traditional gas chromatography. Traditional remote site chromatographs need a calibration gas bottle and a carrier gas bottle about every 6 months. In addition to the consumable costs, the separation columns in the in the GCs have a tendency to get clogged and need replacement. Occasional liquid condensate introduction will not destroy expensive components in an NIR spectrometer. Therefore, you have a new system that is robust, environmentally friendly, and significantly cheaper to own than conventional chromatography or other analytical devices.

Other embodiments may apply these processes and device elements to atmospheric sampling and effluent sampling. Such as in the case of an atmospheric toxicity monitor and environmental monitor for effluent discharge.

In summary the present invention provides a chemical composition analyzer that may be used to optically determine and report chemical compositions associated with natural gases within a gas collection and transmission infrastructure. Once the composition is known, properties of interest can be calculated for the gas. This analyzer includes a number of remote optical sensors which may be used to perform spectroscopic spectrographic analysis in order to determine the chemical composition of the natural gas. Additionally other sensors may be used to measure other physical properties associated with the natural gas. These sensors are tied to a data collection system wherein the output of the remote optical sensors and sensors used to measure the physical properties of the natural gas may be combined and processed in order to determine in a nearly continuous fashion the chemical composition associated with the natural gas at various locations within the gas collection and transmission infrastructure.

Although the present invention is described in detail, it should be understood that various changes, substitutions and alterations can be made hereto without departing from the spirit and scope of the invention as described by the appended claims.

What is claimed is:

1. A method to optically determine and report a chemical composition of a gas comprising:
   measuring, with optical sensors operable to scan a gas over all or substantially all of the near infrared spectrum, the chemical composition of a gas within a gas collection and transmission infrastructure;
   measuring the quantity of an impurity in the gas within the gas collection and transmission infrastructure;
   communicatively coupling the optical sensors to a data gathering location;
   reporting the chemical composition of the gas and the quantity of the impurity in the gas to the data gathering location; and
   processing the reported chemical composition of the gas and the quantity of the impurity in the gas to determine in real time the chemical composition associated with bulk quantities of, and the quantity of the impurity in, the gas within the gas collection and transmission infrastructure.

2. The method of claim 1, wherein the optical sensors perform spectrographic analysis in near infrared.

3. The method of claim 1, wherein the gas consists substantially of natural gas.

4. The method of claim 1, wherein the optical sensors comprise an optical cell coupled to the gas collection and transmission infrastructure.

5. The method of claim 1, wherein a downstream user reconfigures manufacturing processes based on the real time chemical compositions associated with bulk quantities of gas.

6. The method of claim 1, wherein a need for gas collection and transmission infrastructure maintenance is based on the real time chemical compositions associated with bulk quantities of gas.

7. The method of claim 1, wherein the impurity is $H_2S$.

8. A method to schedule maintenance within a gas collection infrastructure, the method comprising:
   measuring, with optical sensors operable to scan a gas over all or substantially all of the near infrared spectrum, the chemical composition of the gas within the gas collection and transmission infrastructure;
   measuring the quantity of an impurity in the gas within the gas collection and transmission infrastructure;
   communicatively coupling the optical sensors to a data gathering location;
   reporting the chemical composition of the gas and the quantity of the impurity in the gas to the data gathering location;
   determining the chemical composition associated with the gas within the gas collection and transmission infrastructure; and
   processing the reported chemical composition of the gas and the quantity of the impurity in the gas to determine a needed maintenance action within the gas collection infrastructure based on the chemical composition of, and the quantity of the impurity in, the gas.

9. The method of claim 1, wherein the gas consists substantially of liquefied natural gas.

10. The method of claim 1, wherein the gas consists substantially of steam.

11. The method of claim 1, wherein the impurity is carbon dioxide.

12. The method of claim 1, wherein the impurity is water.

13. The method of claim 1, wherein the reporting of the chemical composition of the gas includes the transmission of the absorption spectrum of the gas.

14. The method of claim 13, wherein the processing comprises calculating the first derivative of the absorption spectrum of the gas, calculating the first derivative of the absorption spectrum, and dividing the first derivative by the pressure of the gas for normalization.

\* \* \* \* \*